United States Patent [19]

Atlani et al.

[11] 4,316,796
[45] Feb. 23, 1982

[54] PROCESS FOR THE SEPARATION OF DIENIC AND/OR AROMATIC HYDROCARBONS PRESENT IN HYDROCARBON FRACTIONS

[75] Inventors: Martial Atlani, Paris; Roben Loutaty, Le Havre; Claude Wakselman, Villebon sur Yvette; Charles Yacono, Le Havre, all of France

[73] Assignees: Compagnie Francaise de Raffinage; Agence Nationale de Valorisation de la Recherche (ANVAR), both of France

[21] Appl. No.: 186,483

[22] Filed: Sep. 12, 1980

[30] Foreign Application Priority Data

Sep. 14, 1979 [FR] France .............................. 79 23041

[51] Int. Cl.³ .................. C10G 7/08; C10G 21/20; C10G 21/22
[52] U.S. Cl. .................... 208/313; 203/60; 208/330; 585/808; 585/810; 585/856; 585/863
[58] Field of Search ............ 208/313, 323, 330, 348; 203/57, 59, 60; 585/808, 810, 811, 856, 863, 864

[56] References Cited

U.S. PATENT DOCUMENTS 2,225,910 12/1940 Gurd et al. ...................... 208/330
2,385,981 10/1945 Friedman ........................ 208/330
2,433,751 12/1947 Friedman ........................ 208/330
4,170,547 10/1979 Atlani et al. .................... 208/326

*Primary Examiner*—Delbert E. Gantz
*Assistant Examiner*—William Leader
*Attorney, Agent, or Firm*—Scully, Scott, Murphy & Presser

[57] ABSTRACT

Dienic and/or aromatic hydrocarbons are separated from hydrocarbon fractions employing known liquid-liquid extraction and/or extractive distillation procedures and at least one sulfonamide solvent conforming to the general formula

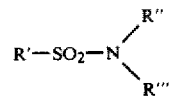

wherein R', R" and 4'" can be linear or branched, saturated or unsaturated, aliphatic groups possessing from 1 to 18 carbon atoms, wherein two or three of groups R', R" and R'" can be identical, wherein one of the groups R" and R'" can be replaced with a hydrogen atom, and wherein at least one of groups R', R" and R'" is unsaturated.

2 Claims, 3 Drawing Figures

PROCESS FOR THE SEPARATION OF DIENIC AND/OR AROMATIC HYDROCARBONS PRESENT IN HYDROCARBON FRACTIONS

BACKGROUND OF THE INVENTION

1. Field of the Invention

The present invention relates to the separation of dienic and/or aromatic hydrocarbons present in hydrocarbon fractions employing sulfonamides; it relates more particularly to the use for this separation, using known techniques of liquid-liquid extraction and/or extractive distillation, of solvents selected from the group constituting the sulfonamides.

2. Description of the Prior Art

As used in the instant specification, the term sulfonamides embraces compounds having in their molecular structure the group $>N-SO_2-$.

Numerous selective solvents for the recovery of hydrocarbons are described in the technical literature. With regard to the dienic hydrocarbons, one can particularly mention N-methylpyrrolidone, acetonitrile and dimethylformamide. One of the possible applications of these solvents is, for example, the selective extraction of isoprene from a cut of hydrocarbons in which the number of carbon atoms is equal to about 5 (this cut of hydrocarbons is commonly referred to as the "C₅ fraction").

Among the known selective solvents for the extraction of aromatic hydrocarbons, one can mention sulfolane, N-methyl-pyrrolidone in aqueous solution, derivatives of morpholine such as N-formylmorpholine or dimethylsulfoxide.

It is also known to use certain saturated aliphatic sulfonamides to separate dienic and/or aromatic hydrocarbons.

In French patent application No. 78 29828 of Oct. 19, 1978, of which the applicants are assignees, there are described for such a use sulfonamides of the general formula:

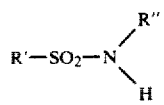

wherein R' and R" are saturated alkyl groups possessing from 1 to 4 carbon atoms.

Sulfonamides of the type

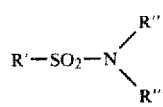

wherein R', R" and R'" are saturated alkyl groups possessing from 1 to 4 carbon atoms are described for the same use in French patent application No. 77 12357 (published as U.S. Pat. No. 2,388,874) and of which applicants are also assignees.

SUMMARY OF THE INVENTION

Applicants have now discovered that it is also possible to employ other sulfonamides as solvents for liquid-liquid extraction and/or extractive distillation to separate dienic and/or aromatic hydrocarbons contained in hydrocarbon fractions.

The object of the present invention is consequently to provide novel solvents for the separation of hydrocarbons.

The present invention has for its object a process for the extraction of dienic and/or aromatic hydrocarbons from hydrocarbon fractions containing them, through known liquid-liquid extraction and/or extractive distillation procedures, said process being characterized in that the solvent employed, optionally in admixture with one or several other substances, is at least one sulfonamide selected from the group consisting of compounds of the general formula:

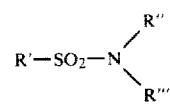

wherein R', R" and R'" can be linear or branched, saturated or unsaturated, aliphatic, i.e., alkyl or alkenyl, groups possessing from 1 to 18 carbon atoms, wherein two or three of groups R', R" and R'" can be identical, wherein one of the groups R" or R'" can be replaced with a hydrogen atom, and wherein at least one of groups R', R" and R'" is unsaturated.

DESCRIPTION OF THE PREFERRED EMBODIMENTS

Applicants have, for example, employed with success the compounds:

N,N-diallyl methanesulfonamide
N,N-methyl allylmethanesulfonamide.

Applicants have discovered the effectiveness of these and other sulfonamides in accordance with the invention in a process for the extraction of dienic and/or aromatic hydrocarbons starting with fractions in which the dienic and/or aromatic hydrocarbons are contained. This effectiveness can be demonstrated by several tests: the selectivity at infinite dilution of a solvent considered with respect to a test hydrocarbon mixture can be measured.

The extraction can also be carried out by a conventional method and the extract and raffinate each analyzed. Such tests are described hereinafter in the examples.

Whatever the extraction procedure utilized, the quantities of solvent employed are, in general, between 0.5 and 5 times the volume of the hydrocarbon charge to be treated but this amount can be greater, particularly if it is desired to reduce the theoretical number of the stages necessary for the extraction.

The solvent utilized can be more or less pure with so-called "commercial" purity being in most cases entirely suitable to achieve extraction. The sulfonamides can be used as much, in admixture with themselves or with other sulfonamides, or yet in admixture with one or several other substances. Extraction can be effected through liquid-liquid extraction or by extractive distillation.

Moreover, the two extraction procedures can be combined, the charge being enriched, in a first stage, for the chemical species to be extracted, by liquid-liquid extraction, then, in a second stage subjected to an extractive distillation which permits the recovery of the chemical species desired.

Three figures of drawings are attached to the instant specification by way of non-limitative illustrations.

In these figures, the recycle streams from the head to the base of the columns have not been represented for the sake of clarity.

Figure 1:
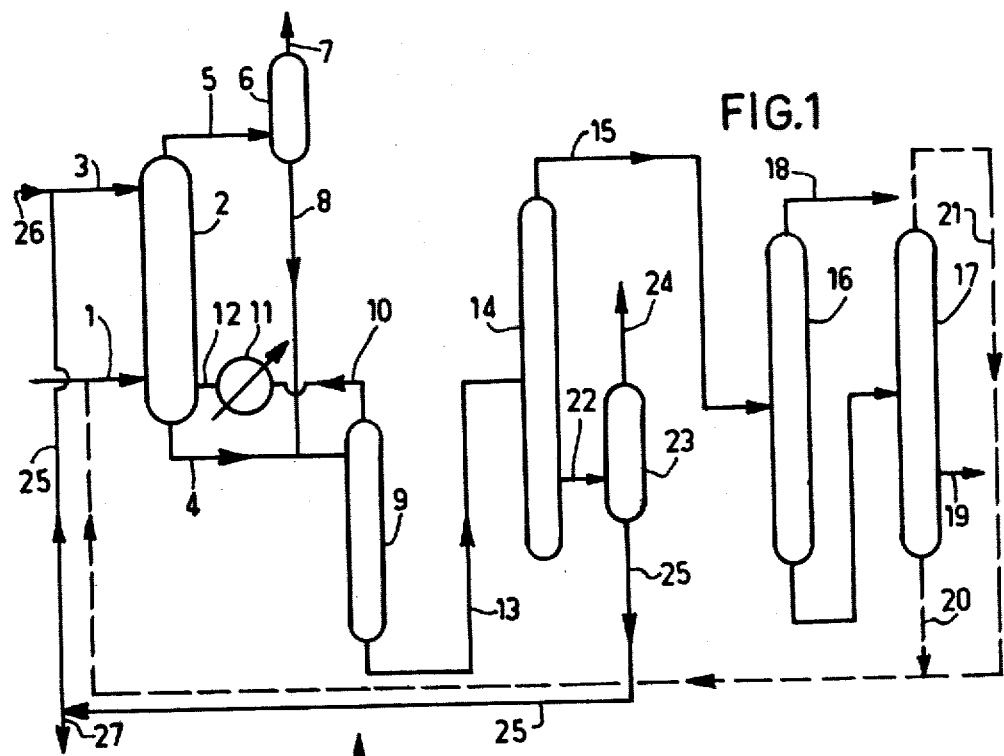
FIGS. 1 and 2 are schematic diagrams illustrating the application of process according to the invention for the continuous extraction of isoprene from a hydrocarbon charge containing five carbon atoms.

In FIG. 1, a feed obtained from the distillation of cracking oil and having been optionally subjected to a preliminary thermal treatment intended to dimerize the cyclopentadiene, is introduced through line 1, in the liquid state, into the lower section of a liquid-liquid extraction column 2. The solvent, containing at least one sulfonamide, is introduced through line 3, in the liquid state, into the upper section of column 2.

The solvent containing the diolefins and a small quantity of pentenes is recovered through line 4, at the base of column 2.

Through line 5, at the top of column 2, is recovered the raffinate comprised principally of the pentanes, the pentenes and light traces of dienes. This raffinate is conveyed through line 5 into a distillation chamber 6, wherein traces of solvent contained therein are removed. The raffinate is evacuated from chamber 6 through line 7 while the solvent is conveyed to line 4 through line 8.

The solvent containing the diolefins and a small quantity of pentenes circulating in line 4 is conveyed into the upper section of rectification column 9.

The vapors recovered at the head of the column 9 through line 10 are liquified in condenser 11; the resulting liquid is introduced through line 12 into the lower section of column 2. The solvent, charged with diolefins, olefins and acetylenic hydrocarbons, is introduced through line 13 into the intermediate section of extractive distillation column 14. At the head of column 14, one recovers, through line 15, a mixture of isoprene and cyclopentene, which one separates by distillation in columns 16 and 17, the isoprene being recovered through line 18 at the head of column 16, and the cyclopentene, by a side discharge from column 17, through line 19. The bottoms, recovered through line 20, and/or the head vapors, recovered in line 21 of column 17, can be recycled in the charge to column 2.

Through line 22, there is laterally discharged from column 14 a gaseous stream principally comprising the pentadienes, cyclopentadiene and the acetylenic hydrocarbons. The solvent vapors are separated from the hydrocarbons by distillation in chamber 23.

The hydrocarbons are recovered at the top of chamber 23 through line 24. Solvent recovered at the base of chamber 23 through line 25 is recycled to column 2 through line 3. Fresh solvent can be introduced into line 25 through line 26 and spent solvent can be discharged through purge 27.

Figure 2:
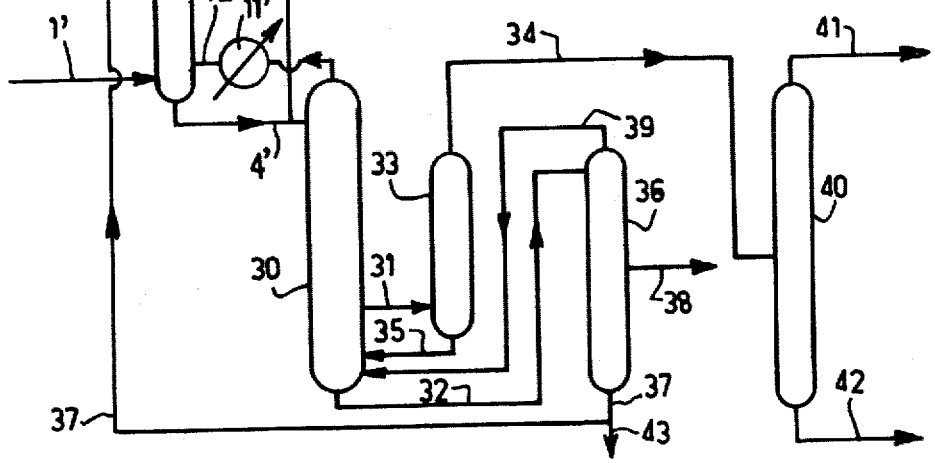

In another embodiment of the invention schematically represented in FIG. 2, for which the elements identical to those of FIG. 1 have been identified by the same reference numerals bearing a prime mark, extraction column 2' is identical to column 2 of FIG. 1, but rectification column 30 is more effective than column 9, the latter permitting the side withdrawal, through line 31, of a mixture of vapors of isoprene and cyclopentene charged with solvent and, at the base, through line 32, the major part of liquid solvent charged with less volatile hydrocarbons in the presence of solvent, that is, cyclopentadiene, the pentadienes and the acetylenic hydrocarbons. The vapors of solvent are separated from isoprene and cyclopentene by distillation in chamber 33.

Isoprene and cyclopentene are recovered through line 34, the solvent being returned to column 30 through line 35. The bottoms from column 30 are introduced through line 32 into apparatus for the recovery of solvent constituting a column 36; the solvent recovered through line 37, at the base of column 36, being recycled in column 2' through line 3'; column 36 comprising a side withdrawal point 38, through which there is withdrawn a mixture of cyclopentadiene, pentadienes and acetylenic hydrocarbons. At the head of column 36 is recovered a vapor phase, through line 39, which is recycled in the lower section of column 30. Line 34 feeds a fractionation column 40, from which one recovers isoprene, at the head, through line 41, and cyclopentene, at the base, through line 42. Fresh solvent can be introduced into line 37 through line 44 and spent solvent can be withdrawn through purge 43.

Figure 3:
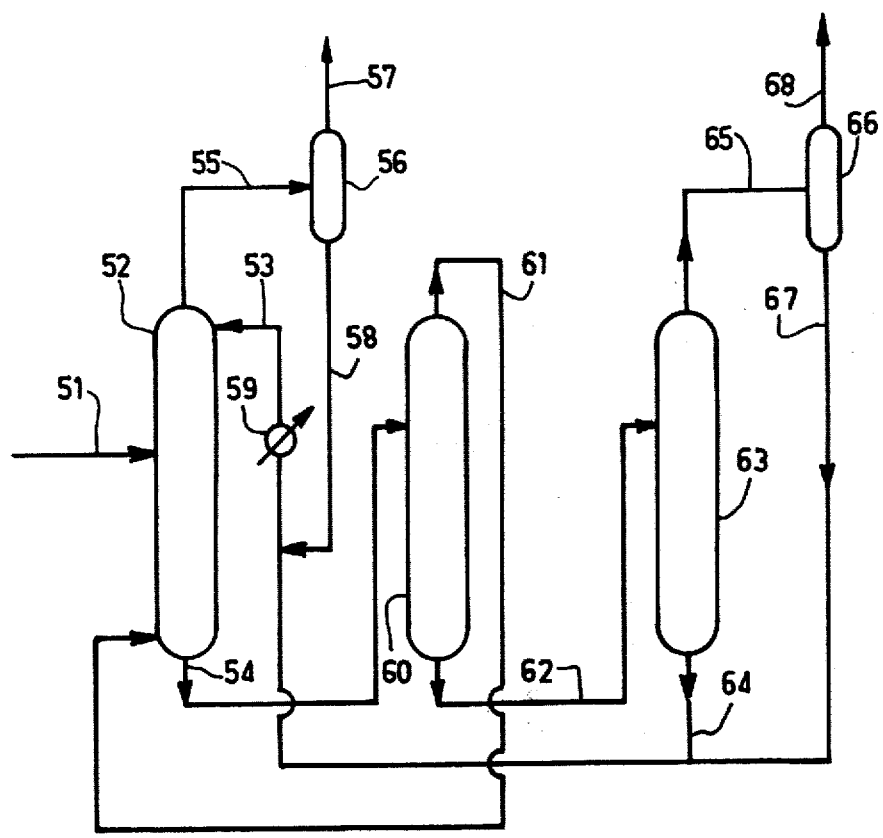
FIG. 3 is a schematic diagram illustrating the application of the process according to the invention for the continuous extraction of aromatic hydrocarbons from a charge in which they are contained.

Referring to FIG. 3, a charge, for which one desires to separate the aromatic hydrocarbons, obtained by reforming a petroleum fraction, is introduced through line 51 into the intermediate section of extraction column 52. The solvent, containing at least one sulfonamide, is introduced through line 53 in the liquid state into the upper section of column 52. One recovers through line 54, at the base of column 52, the solvent containing the aromatic hydrocarbons and a certain quantity of non-aromatic hydrocarbons. The raffinate comprising non-aromatic hydrocarbons is recovered through line 55 at the head of column 52.

This raffinate is introduced through line 55 into distillation chamber 56 where it is separated from traces of solvent contained therein. The raffinate is withdrawn from chamber 56 through line 57. The solvent recovered from line 58 is recycled to column 52 through line 53 after passage through condenser 59. The solvent containing the aromatic hydrocarbons and a certain quantity of non-aromatic hydrocarbons recovered through line 54 is conveyed to the intermediate section of extraction distillation column 60. At the head of column 60, is recovered, through line 61, the non-aromatic hydrocarbons and a small quantity of aromatic hydrocarbons which are recycled to the base of column 52. The solvent containing the aromatic hydrocarbons is recovered through line 62 at the base of column 60. The solvent containing the aromatic hydrocarbon is conveyed into the middle section of column 63 operated under reduced pressure. The solvent is recovered at the base of column 63, through line 64, and is recycled to column 52.

At the top of column 63, through line 65, are recovered the aromatic hydrocarbons containing traces of solvent, which are separated in distillation chamber 66. At the base of chamber 66, through line 67, is recovered the solvent, which is recycled to column 52. The aromatic hydrocarbons are recovered at the top of chamber 66 through line 68.

The invention is illustrated, moveover, by the examples which follow and which are of non-limitative character.

Examples 1 and 2 illustrate the use of sulfonamides according to the present invention for the extraction of aromatic hydrocarbons from a mixture containing them.

Example 3 illustrates the use of sulfonamides according to the invention for the extraction of dienic hydrocarbons from a mixture containing them.

EXAMPLE 1

This example illustrates the utilization of solvents according to the invention for the extraction of aromatic hydrocarbons present in mixtures of hydrocarbons by extractive distillation, or by liquid-liquid extraction, or by a combination of these two procedures.

There was determined, for two solvents in accordance with the invention, namely, for N,N-methyl allylmethanesulfonamide and N,N-diallyl methanesulfonamide the selectivity at infinite dilution at 50° C. for two binary mixtures of hydrocarbons having neighboring boiling points, i.e., a mixture of benzene and 2,4-dimethylpentane and a mixture of benzene and cyclohexane.

The selectivity at infinite dilution for a mixture of hydrocarbons for which the extractive distillation and/or the liquid-liquid extraction is desired is defined as the ratio of the coefficients of activity at infinite dilution of two hydrocarbons in the same solvent. The separation is proportionately more effective as the selectivity at infinite dilution is greater. See, "Propriétés thermodynamiques des solution infiniment diluées d'hydrocarbures dans les solvants polaires" ("The Thermodynamic Properties of Infintely Diluted Hydrocarbons in Polar Solvents") by P. Vernier, C. Raimbault and H. Renon, *Journal de Chimie physique*, 1969, V. 66, No. 3, pp. 429 to 436.

The coefficients of activity at infinite dilution were measured by the "exponential dilution" method. See, "Accurate measurement of activity coefficients at infinite dilution by inert gas stripping and gas chromatography" by J. C. Leroi, J. C. Masson, H. Renon, J. F. Fabries and H. Sannier, *Ind. Eng. Chem. Process Des. Dev.*, 1977, V. 16, No. 1, pp. 139 to 144.

The results are set forth in Table I which follows:

TABLE 1

| Hydrocarbons | | | Coefficients of activity at infinite dilution of 50° C. | | Selectivites at infinite dilution at 50° C. with respect to benzene | |
|---|---|---|---|---|---|---|
| Name | Boiling point at 760 mm Hg (°C.) | | in N,N-methyl allylmethane-sulfonamide | in N,N-diallyl methanesulfon-amide | in N,N-methyl allymethane-sulfonamide | in N,N-diallyl methanesulfon-amide |
| Benzene | 80.1 | | 1.37 | 1.04 | 1 | 1 |
| Cyclohexane | 80.7 | | 6.76 | 4.79 | 4.93 | 4.61 |
| 2,4-dimethyl-pentane | 80.5 | | 9.85 | 8.95 | 7.19 | 8.61 |

The values obtained for the selectivities at infinite dilution show that the separations are effective. Benzene can therefore be extracted from its admixture with 2,4-dimethylpentane or cyclohexane employing solvents according to the invention.

EXAMPLE 2

This example illustrates the utilization of solvents in accordance with the invention for the extraction of an aromatic hydrocarbon by liquid-liquid extraction. In a separatory funnel, a ternary mixture of benzene (hereinafter referred to as the solute), n-heptane (hereinafter referred to as the diluent) and a solvent according to the invention is prepared.

Following agitation, the contents of the separatory funnel are left to stand at a temperature of 20° C. There is thus obtained two phases. The results of the test are set forth in Table 2 hereinafter in which: the coefficient of division is the ratio:

$$\frac{\text{mass fraction HC (solute or diluent) in the extract}}{\text{mass fraction of the same HC in the raffinate}}$$

HC signifying hydrocarbon, the separation factor is the ratio:

$$\frac{\text{coefficient of division of the solute}}{\text{coefficient of division of the diluent}}$$

The mass fractions of the ternary mixture were determined by weighing, those of the extract and the raffinate by gaseous phase chromatography.

| Ternary mixture at 20° C. | Composition of the mixture in % by weight | Composition of the extract in % by weight | Composition of the raffinate in % by weight | Co-efficients of Divison | Separation factor |
|---|---|---|---|---|---|
| benzene | 17.60 | 16.26 | 20.91 | 0.778 | 8.47 |
| n-heptane | 32.80 | 6.94 | 75.59 | 0.092 | |
| N,N-methyl-allylmethane-sulfonamide | 49.60 | 76.80 | 3.50 | | |

The values obtained for the separation factors show that the separations are effective. Benzene can therefore be extracted from its admixture with n-heptane employing solvents according to the invention.

EXAMPLE 3

This example illustrates the utilization of solvents according to the invention for the extraction of dienic hydrocarbons from mixtures of hydrocarbons containing them, by extractive distillation, by liquid-liquid extraction or by a combination of these two techniques.

There was determined, for two solvents according to the invention, the selectivity at infinite dilution at 30° C. for two binary mixtures of hydrocarbons having neighboring boiling points, i.e., a mixture of isoprene and pentane and a mixture of isoprene and 2-methylbutene-2.

The selectivity at infinite dilution is defined and determined in the same manner as in Example 1.

The results are set forth in Table 3 below.

TABLE 3

| Hydrocarbons | | Coefficient of activity at infinite dilution at 30° C. | | Selectivities at infinite dilution at 30° C. with respect to isoprene | |
| --- | --- | --- | --- | --- | --- |
| Name | Boiling point at 160 mm Hg (mm) | in N,N-methyl allyl-methane sulfon-amide | in N,N-diallyl methane-sulfon-amide | in N,N-methyl allyl-methane-sulfon-amide | in N,N-diallyl methane-sulfon-amide |
| Isoprene | 34.1 | 3.03 | 2.03 | 1 | 1 |
| 2-methyl-butene-2 | 38.6 | 5.69 | 3.43 | 1.88 | 1.69 |
| n-pentane | 36.1 | 11.88 | 6.73 | 3.92 | 3.31 |

The values obtained for the selectivities at infinite dilution show that the separations are effective. Isoprene can therefore be extracted from its admixtures with n-pentane or 2-methylbutene-2 employing solvents according to the invention.

What is claimed is:

1. A process for the solvent extraction of dienic and/or aromatic hydrocarbons present in hydrocarbon fractions employing liquid-liquid extraction and/or extractive distillation, said process being characterized in that the solvent comprises at least one sulfonamide of the general formula

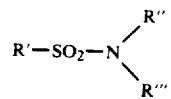

wherein R', R" and R'" can be linear or branched, saturated or unsaturated, aliphatic groups possessing from 1 to 18 carbon atoms, wherein two or three of groups R', R" and R'" can be identical, wherein one of the groups R" or R'" can be replaced with a hydrogen atom, and wherein at least one of groups R', R" and R'" is unsaturated.

2. Process according to claim 1, characterized in that the sulfonamide is selected from the group consisting of N,N-diallyl methanesulfonamide and N,N-methyl allyl-methanesulfonamide.